(12) United States Patent
Guger et al.

(10) Patent No.: US 10,390,722 B2
(45) Date of Patent: Aug. 27, 2019

(54) METHOD FOR QUANTIFYING THE PERCEPTIVE FACULTY OF A PERSON

(71) Applicants: Christoph Guger, Piberbach (AT); Guenter Edlinger, Graz (AT)

(72) Inventors: Christoph Guger, Piberbach (AT); Guenter Edlinger, Graz (AT)

( * ) Notice: Subject to any disclaimer, the term of this patent is extended or adjusted under 35 U.S.C. 154(b) by 319 days.

(21) Appl. No.: 15/106,884

(22) PCT Filed: Sep. 25, 2014

(86) PCT No.: PCT/AT2014/050218
§ 371 (c)(1),
(2) Date: Jun. 21, 2016

(87) PCT Pub. No.: WO2015/058223
PCT Pub. Date: Apr. 30, 2015

(65) Prior Publication Data
US 2016/0360992 A1    Dec. 15, 2016

(30) Foreign Application Priority Data
Oct. 21, 2013   (AT) .................................. 50676/2013

(51) Int. Cl.
*A61B 5/0484* (2006.01)
*A61B 5/00* (2006.01)
(Continued)

(52) U.S. Cl.
CPC ........ *A61B 5/04845* (2013.01); *A61B 5/0484* (2013.01); *A61B 5/04842* (2013.01);
(Continued)

(58) Field of Classification Search
CPC .............................. A61B 5/0484; A61B 5/16
See application file for complete search history.

(56) References Cited

U.S. PATENT DOCUMENTS 5,406,956 A * 4/1995 Farwell ................ A61B 5/0478
600/544
9,339,227 B2   5/2016 D'arcy et al.
(Continued)

FOREIGN PATENT DOCUMENTS

DE       4226672 A1    1/1993
WO    2011160222 A1   12/2011

OTHER PUBLICATIONS

Vlek R J et al: "Sequenced subjective accents for braincomputer interfaces", Journal of Neural Engineering, Institute of Physics Publishing, Bristol, GB, vol. 8, No. 3, Apr. 4, 2011 (Apr. 4, 2011), p. 36002, XP020205962, ISSN: 1741-2552, DOI: 10.1088/1741-2560/8/3/036002.
(Continued)

*Primary Examiner* — David L Lewis
*Assistant Examiner* — Eric M Thomas
(74) *Attorney, Agent, or Firm* — Laurence A. Greenberg; Werner H. Stemer; Ralph E. Locher (57) ABSTRACT

Differently perceptible types of stimuli are applied to the a test subject and the test subject is set intellectual tasks which, in the presence of a stimulus, are intended to be performed according to the nature of this stimulus. In a plurality of test steps a particular type of stimulus is chosen from the set of possible types of stimuli and applied to the person. During or after the application of the respective stimulus, EEG data of the person are determined and recorded preferably within 1 to 10 seconds. Classification analysis is used to determine a measure of whether the EEG data assigned to a defined stimulus are distinguishable from the EEG data assigned to a stimulus of a different type. The measure of the distinguishability of the EEG data of different stimuli is used as a measure of the perceptive faculty.

19 Claims, 3 Drawing Sheets

(51) Int. Cl.
*A61B 5/16* (2006.01)
*G09B 5/06* (2006.01)
*G09B 19/00* (2006.01)

(52) U.S. Cl.
CPC .............. *A61B 5/16* (2013.01); *A61B 5/7264* (2013.01); *A61B 5/7267* (2013.01); *A61B 5/742* (2013.01); *G09B 5/06* (2013.01); *G09B 19/00* (2013.01)

(56) References Cited

U.S. PATENT DOCUMENTS

| | | | |
|---|---|---|---|
| 2002/0107454 A1* | 8/2002 | Collura | A61B 5/0531 600/544 |
| 2005/0017870 A1 | 1/2005 | Allison et al. | |
| 2007/0049844 A1* | 3/2007 | Rosenfeld | A61B 5/04842 600/544 |
| 2009/0062679 A1 | 3/2009 | Tan et al. | |
| 2009/0156954 A1* | 6/2009 | Cox | A61B 5/048 600/544 |

OTHER PUBLICATIONS

F. Bernasconi et al: "Noise in Brain Activity Engenders Perception and Influences Discrimination Sensitivity", Journal of Neuroscience, vol. 31, No. 49, Dec. 7, 2011 (Dec. 7, 2011), pp. 17971-17981, XP055159341, ISSN: 0270-6474, DOI: 10.1523/JNEUROSCI.3715-11.2011.

Jan-Niklas Antons et al: "Analyzing Speech Quality Perception Using Electroencephalography", IEEE Journal of Selected Topics in Signal Processing, IEEE, US, vol. 6, No. 6, Oct. 1, 2012 (Oct. 1, 2012), pp. 721-731, XP011460707, ISSN: 1932-4553, DOI: 10.1109/JSTSP.2012.2191936.

Guger C et al: "Real-Time EEG Analysis with Subject-Specific Spatial Patterns for a Brain-Computer Interface (BCI)", IEEE Transactions on Rehabilitation Engineering, IEEE Inc. New York, US, vol. 8, No. 4, Dec. 1, 2000 (Dec. 1, 2000), XP011053741, ISSN: 1063-6528.

T. K. Guttorm et al: "Event-related potentials in newborns with and without familial risk for dyslexia: principal component analysis reveals differences between the groups", Journal of Neural Transmission, vol. 110, No. 9, Sep. 1, 2003 (Sep. 1, 2003), pp. 1059-1074, XP055159289, ISSN: 0300-9564, DOI: 10.1007/s00702-003-0014-x.

C. M. Bishop, "Neural Networks for Pattern Recognition", Clarendon Press Oxford 1995.

Wissel T et al., "Hidden Markov model and support vector machine based decoding of finger movements using electrocortigraphy" Journal of Neural Engineering 10, (2013), 056020.

Stephen Huff J et al: "Emergency Neurological Life Support: Approach to the Patient with Coma", Neurocritical Care, Humana Press Inc, New York, vol. 17, No. 1, Aug. 30, 2012 (Aug. 30, 2012), pp. 54-59, XP035114475,ISSN: 1556-0961, DOI: 10.1007/S12028-012-9755-4.

Colon E et al: "Steady-state evoked potentials to study the processing of tactile and nociceptive somatosensory input in the human brain", Neurophysiologie Clinique—Clinical Neurophysiology, vol. 42, No. 5, Jun. 22, 2012 (Jun. 22, 2012), pp. 315-323, XP028944018,ISSN: 0987-7053, DOI: 10.1016/J.NEUCLI.2012.05.005.

* cited by examiner

METHOD FOR QUANTIFYING THE PERCEPTIVE FACULTY OF A PERSON

BACKGROUND OF THE INVENTION

Field of the Invention

The invention relates to a method for quantifying the perceptive faculty of a person.

Various measuring methods that can be used for detecting different mental activities of a person are known from the prior art. Also known from the prior art are individual brain computer interfaces, with which the processes taking place inside the brain of a person can be determined, further processed and also visually depicted in various ways.

Such interfaces are of considerable importance if the person concerned has no other available possibilities for communication, such as language, gestures etc. Essential background of the invention is the investigation of patients at the late stage of neurological disorders, for example at the late stage of amyotrophic lateral sclerosis (ALS), or else patients with awareness disorders, to find the level of their individual subjective perceptive faculty at a particular point in time. The determination of these faculties is of extremely great relevance for the patient concerned since, depending on the personal perceptive faculty, communication possibilities adapted to the patient can be used.

A quantification of the perceptive faculty makes it possible to determine to what extent this person, referred to hereinafter as the test subject, is still capable of communicating with the world around them. It is additionally advantageous if the successes in learning that are necessarily gained during the quantification of the perceptive faculty can also be used by the test subject for subsequent computer-aided communication.

The prior art discloses methods that can determine classifications of EEG data exclusively on the basis of already existing measured values. However, such methods are sometimes highly inconclusive, since it is very likely with EEG data for there to be individual differences between individual test subjects.

BRIEF SUMMARY OF THE INVENTION

The present invention addresses the problem of providing a quick and simple method for quantifying the perceptive faculty that makes effective ascertainment of the perceptive faculty possible, and is to the greatest extent independent of individual differences between individual test subjects.

The invention solves the problem by the features as claimed.

In the case of a method for quantifying the perceptive faculty of a person, it is proposed according to the invention
a) wherein a set of at least two possible differently perceptible types of stimuli that can be applied to the test subject is prescribed, and
b) the test subject is set mental activities which, in the presence of a stimulus, are intended to be performed according to the nature of this stimulus,
c) wherein a plurality of test steps are carried out, wherein for each of the test steps
a respective type of stimulus is chosen from the set of possible types of stimuli, in particular according to random criteria,
a stimulus of the respectively chosen type of stimuli is applied to the person,
within a time range before, during or after the application of the respective stimulus, EEG data of the person are determined and recorded, wherein the time range preferably has a duration of 1 to 10 seconds, and
the respectively determined EEG data or data derived therefrom are assigned to the respective type of stimulus,
d) wherein classification analysis is used to determine a measure of whether the EEG data assigned to a particular stimulus are distinguishable from the EEG data assigned to a stimulus of a different type, and
e) wherein the measure of the distinguishability of the EEG data of different stimuli is used as a measure of the perceptive faculty.

The invention has the major advantage that the perceptive faculty of a person is quantifiable independently of whether this person is capable of actually performing motor actions. In addition, it is of advantage that the present test can be easily adapted to different test conditions, in that the person is set different mental activities, which in each case lead to different results in the EEG data. Depending on the person, individually different mental activities can also be used for the quantification, in order to obtain a value that is as meaningful as possible. Also, the test can be adapted to different additional sensory disorders of the person.

A simple method for determining the measure provides that the measure is determined by investigating with what probability the application of the classification analysis to the individual EEG data assigned to the types of stimuli in each case suggests the correct stimulus.

A particularly simple embodiment of the invention, for which the only prerequisite is the functional faculty of hearing, provides that the set of types of stimuli is prescribed by different sounds, in particular of differing duration, frequency and volume, in humanly audible frequencies and the respective sound is played to the person.

A further embodiment of the invention, for which the prerequisite is a slight tactile sensitivity, provides that the set of types of stimuli comprises exposure to vibrations of different parts of the body and/or of differing intensity and/or duration, which are applied to the person by means of vibration units.

A further embodiment of the invention, for which the prerequisite is a visual sensitivity, provides that the set of types of stimuli comprises visual stimuli for one eye or both eyes and/or of differing intensity and/or duration, which are applied to the person by means of a screen or by means of lighting means.

A further embodiment of the invention, for which the prerequisite is a sensitivity to electrical stimulus, provides that the set of types of stimuli comprises electrical stimuli to different parts of the body and/or of differing intensity and/or duration, which are applied to the person by means of electrical stimulators.

Mental activities which are particularly distinctive and can be easily carried out by test subjects and which achieve particularly meaningful results in connection with the present invention are for example:
counting or calculating,
thinking of movements of body parts, in particular extremities of the right or left half of the body, preferably the arms or hands.

A particularly advantageous preprocessing of the EEG data comprising a multiplicity of EEG signals and EEG channels provides that an assessment of the recorded EEG data is performed, in that the individual EEG data of the individual EEG channels that were recorded at the same point in time are respectively combined to form a signal vector, that a number of, in particular four, weight vectors, which have the same number of elements as the signal vectors, is prescribed, that, for each point in time, the respective scalar product of the determined signal vector is created with each of the weight vectors and the respectively created scalar products are assigned to the respective weight vector, that among the scalar products assigned to respectively the same weight vector the variance over a prescribed time range is respectively determined and assigned to the weight vector, that the individual variances, possibly also a further, prescribed summand, are weighted with weight values of a further weight vector and summated, and that the sum thus obtained or a series of sums thus recorded one directly after the other is taken as a test value to form the basis for the classification analysis.

A particularly advantageous, individual adaptation to the respective person provides that the weight vectors and the weight values, and possibly the further summand, are adapted to the respective person, so that the measure determined in the classification analysis is maximized, in particular in that, starting from prescribed starting values, the weight vectors, the weight values, and possibly the further summand, are iteratively adapted until the classification analysis on the basis of the already determined test data produces a maximum measure of distinguishability.

In order to avoid disturbances of the determined EEG signals and to achieve a particularly high distinguishability between the individual EEG signals, it may be provided that, before the assessment by means of classification analysis, the EEG data are subjected channel by channel to a bandpass filtering, wherein the filtered signal contains frequencies between 8 Hz and 30 Hz, in particular exclusively.

In order to achieve an advantageous interaction with the test subject to be investigated and in order to give direct feedback to the test subject to be investigated, it may be provided that the EEG data or the data taken as a basis for the classification analysis, in particular the results of an averaging, the evoked potentials derived from the EEG data or the EEG data after carrying out an event-related desynchronization or the EEG data, are displayed, preferably to the person and/or to an operator conducting the method.

A particularly quick, simple and efficient implementation can be carried out if the measure of whether the EEG data assigned to a particular stimulus are distinguishable from the EEG data assigned to a stimulus of a different type are carried out by means of one of the following types of classification analysis:

discriminance analysis, in particular linear discriminance analysis, support vector machines, neural networks.

In order to be able to eliminate day- and week-related fluctuations of individual test subjects, it may be provided that the method is carried out on a number of days, in particular successive days, possibly repeatedly, in particular with the same stimuli, wherein the measure of the perceptive faculty of the person is determined separately for each day and the measure that indicates the greatest perceptive faculty is used as the measure of the perceptive faculty of the person.

In order to be able to perform a communication after carrying out the quantification of the perceptive faculty with simple means and be able to make further advantageous use of the data achieved in the course of the quantification, it may be provided that, once the measure of the perceptive faculty has been determined, for purposes of communication, in particular for answering yes and no to questions, the person is set the mental activities that were previously used, that the person performs the mental activities in answer to the question asked, that, within prescribed time ranges during or after the question, EEG data of the person are determined and recorded, that the respectively recorded EEG data are classified by means of the classification analysis previously carried out, and that the respectively determined results of the classification are used as communication contents and are possibly kept available.

Methods for carrying out the invention may be advantageously carried out by means of computers. The invention also relates to a data carrier, on which a method for carrying out a method according to the invention as claimed in one of the preceding claims is stored.

An exemplary embodiment of the invention and several advantageous developments of the same are presented in more detail below.

DESCRIPTION OF THE INVENTION

Figure 1:
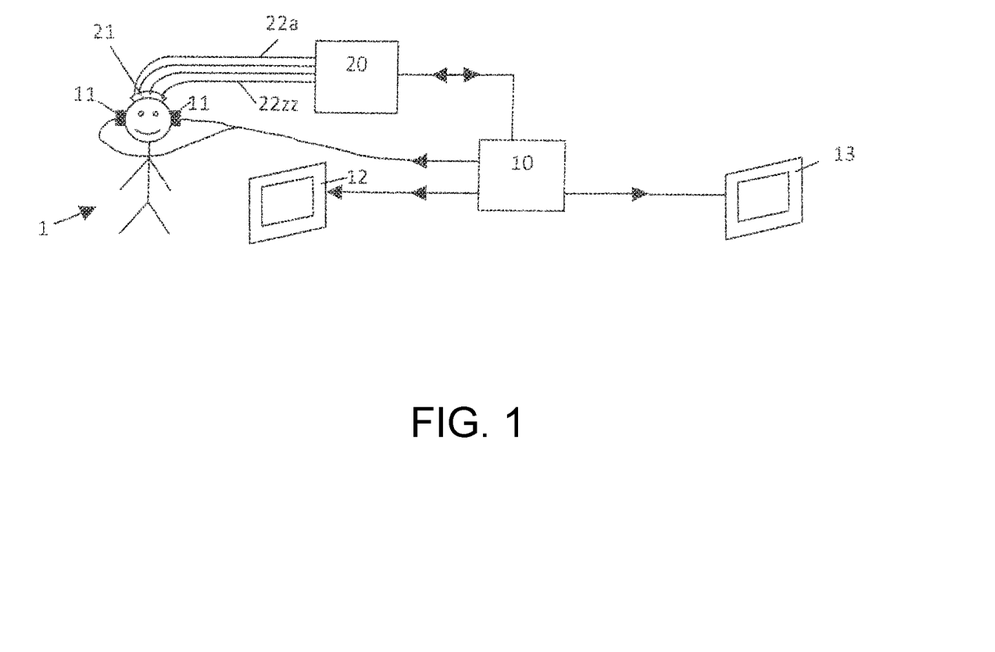
FIG. 1 schematically shows an example of an arrangement for carrying out a method according to the invention.

FIG. 1 shows a person, referred to hereinafter as the test subject 1, whose perceptive faculty is to be quantified. For this, an EEG cap 21, which is connected to a test unit 20 by means of in each case an EEG cable connections 22a, . . . , 22zz, has been placed on the person. Furthermore, headphones 11, by means of which acoustic stimuli S, for example in the form of sounds or series of sounds, can be applied to the test subject 1, have been placed on the person. The headphones 11 and the test unit 20 are connected to a control unit 10, which controls the emission of the stimuli S and to which the test values of the test unit 20 are transmitted. With the control unit 10, the test unit 20 can be configured and adapted to the respective test subject 1.

At the beginning of the method, a set of different stimuli S is established. In a preferred embodiment of the invention, sounds of differing pitch, which can be played to the test subject 1 by means of a loudspeaker 11 or headphones 11, are established as stimuli S. In order to make the quantification as easy as possible for the test subject 1, in the exemplary embodiment presented by way of example only two different pitches are prescribed as possible stimuli S.

It goes without saying, however, that other sets of stimuli S can also be used within the scope of the invention.

On the one hand, it is possible that the test subject 1 can only perceive certain characteristics of noises, such as duration, frequency and volume, to a limited extent. The set of types of stimuli S may consequently also be established by prescribing different sounds, in particular of differing duration, frequency and volume, at humanly audible frequencies and playing the respective sound to the test subject.

On the other hand, it may well be of advantage for more accurate quantification to use more than two different stimuli S. Also, when the test subject 1 has a particular known deficiency, it may also happen that the person cannot perceive the stimulus S for other reasons, for example there is the possibility that, although the test subject 1 is fully conscious, he or she has a disorder of the auditory canals or the auditory nerve and for this reason is unable to interpret adequately an audible stimulus as a stimulus S.

It is therefore also possible to use as stimuli S other visually, electrically and tactically or otherwise perceptible stimuli. The set of types of stimuli S may for example be applied to the test subject in the form of exposure to vibrations of different parts of the body and/or of differing intensity and/or duration by means of vibration units.

In a further step to be performed at the beginning of the method, the test subject 1 is notified which reactions he or she has to carry out in response to the respective stimuli S. This notification may take place in various ways, for example by a declaration in the form of a notification by voice or by presenting the desired procedure on a screen 12.

A possible task for the test subject 1 is for example the instruction to think of the right hand when there is a high-pitched sound and to think of the left hand when there is a low-pitched sound. Alternatively, a possible task may be for the person to count to himself or herself when a vibration unit applies a tactile stimulus in a prescribed area of the body. Adapted to different capabilities of the test subject 1 and to the knowledge of prior sensory impairments, a task that is adapted to the test subject 1 can be set.

Depending on the progress made in the quantification method, differentiated mental activities may also be demanded, for example thinking of one of a number of previously prescribed areas of the body as a reaction to a respective stimulus S from a prescribed set of stimuli S.

Figure 2:
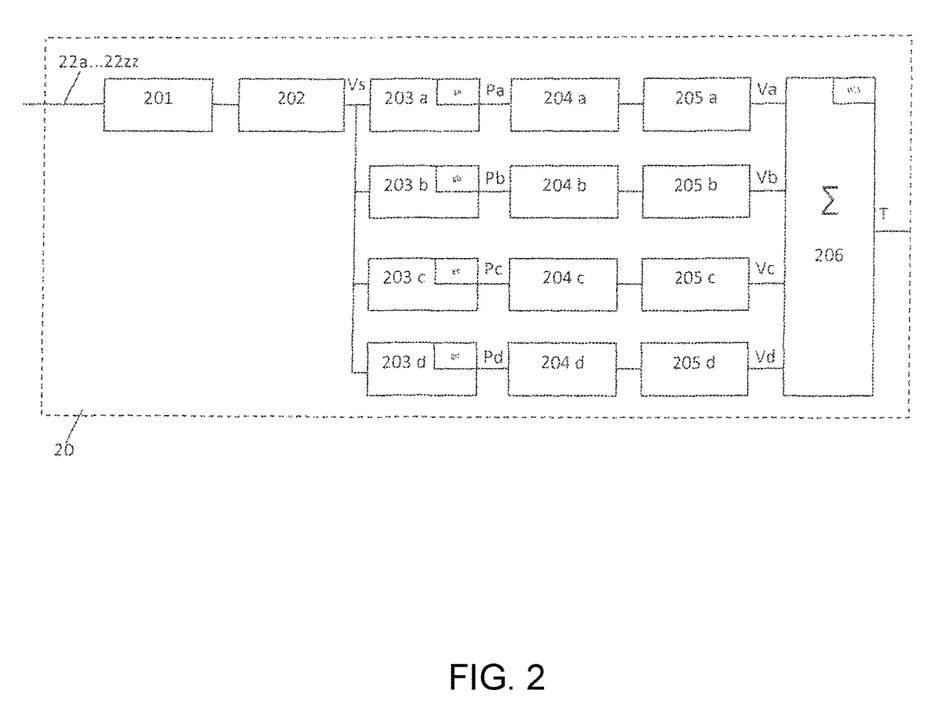
FIG. 2 shows the procedure for the further processing of EEG data up to the determination of test values.

Before carrying out individual test steps of the method, a number of EEG electrodes are placed onto the head of the test subject 1. An arrangement of probes comprising electrodes, in the present example comprising 27 electrodes, is placed onto the head of a test subject 1. The individual discharges determined from the electrodes are passed to an amplifier unit 201, amplified and digitized.

Before carrying out the test, the individual stimuli S are applied to the test subject 1, in order to make the person familiar with all of the stimuli S. In the present example, both the high-pitched sound and the low-pitched sound are played to the test subject 1, and the person is subsequently notified which reaction is expected from him or her, specifically that he or she is to think of the extremities of his or her right hand or a movement of the extremities of the right hand when a high-pitched sound is detected and that he or she is to think of the extremities of his or her left hand or a movement of the extremities of the left hand when a low-pitched sound is detected.

In the method described here, 50 test steps are carried out one after the other on each of three successive days. In each individual test step, a type of stimulus S is respectively chosen here from the set of stimuli S on the basis of random criteria. A random unit 101 (FIG. 3) chooses a type of stimulus S and transmits a relevant selection signal to a stimulus unit 102, which transmits the stimulus S to the headphones 11 in the form of an analog electrical signal.

There is the possibility here of determining the measure of the perceptive faculty of the test subject 1 on several days separately for the respective day and using the measure that indicates the greatest perceptive faculty as the measure of the perceptive faculty of the test subject overall.

In the present exemplary embodiment, in the first test step the test subject 1 is played a high-pitched sound for one second. The test subject 1 detects the high-pitched sound as such and, while the high-pitched sound is playing or thereafter, correspondingly thinks of his or her right hand. Within a time window of 10 seconds, all of the EEG channels are used for further investigation. The beginning of this time window may be before, during or after the stimulus. In the present example, the time window begins 100 ms before the beginning of the stimulus.

The individual EEG signals are sampled at a sampling rate of 256 samples per second with an analog-digital converter 201 (FIG. 2) and converted into digital signals, so that altogether 256×10×27=69, 120 individual sample values are obtained over 10 seconds for characterizing the thoughts of the test subject.

The sample values obtained from the EEG measurement are subjected channel by channel to a bandpass filtering 202. In this case, a filtering that frequency components of the signal that are less than 8 Hz and greater than 30 Hz are strongly attenuated is performed before or after the sampling.

In principle, individual values derived from the entirety of the signal, for example a signal vector s comprising all of the individual signal values determined channel by channel of the EEG signal, may be used for a discriminance analysis. A discriminance analysis carried out in such a way may in principle be further used for quantifying the perceptive faculty.

However, the present preferred embodiment of the invention provides a simplification, which makes it possible for the method to be carried out with a much lower consumption of resources. For this, all of the signal values of the individual EEG channels recorded at the same point in time are combined to form a common signal vector s. In the present example, the signal vectors s respectively comprise 27 individual signal values, specifically one per EEG channel.

Furthermore, four individual weight vectors $g_a, \ldots, g_d$, which have the same magnitude as the signal vectors s, are determined for the respective person. In the present example, the weight vectors respectively have 27 elements or entries. For each individual recording time or sampling time during the time window, a respective scalar product $p_a$, $p_b$, $p_c$, $p_d$ of the determined signal vector s is created with each of the weight vectors, $g_a \ldots, g_d$ by a respective weighting unit 203a, 203b, 203c, 203d. In this advantageous embodiment of the invention, the last-created, for example 5 to 100, scalar products $p_a, p_b, p_c, p_d$ are respectively stored separately for the respective weight vector $g_a, \ldots, g_d$ in downstream buffer memories 204a, 204b, 204c, 204d. Subsequently, the variance $v_a, v_b, v_c, v_d$ is respectively determined for these scalar products $p_a, p_b, p_c, p_d$ lying in the buffer memories 204a, 204b, 204c, 204d. All of these variances $V_a, v_b, v_c, v_d$ determined at a point in time are respectively transmitted to a downstream weighting unit 206. This weighting unit 206 forms a weighted sum of the individual variances $v_a, v_b, v_c, v_d$, each of the variances being respectively used with a weight value $w_a, w_b, w_c, w_d$ from a further weight vector w. The weighting unit 206 possibly also adds a further summand s, so that a scalar value T is present at the output of the weighting unit 206.

The series of values determined within the time window is referred to hereinafter as the test value and is transmitted from the test unit 20 to the control unit 10 and assigned by the latter to the respective type of stimulus S. The weight vectors $g_a, \ldots, g_a$, the further weight vector W and the further summand S are referred to hereinafter as individual data and are determined separately for each test subject 1.

The actual determination of the individual data $g_a, \ldots, g_d$, w, s takes place in the present exemplary embodiment in an optimizing method and is described in more detail below, and advantageously takes place after carrying out fewer test steps and can possibly be repeated for adaptation to successes in training the test subject 1.

With this advantageous method it can be ensured that the discriminance analysis can be performed on a numerically small scale. In particular, 20250 scalar values need not be evaluated, but just one test value T with a small number of scalar values, whereby a drastically simplified discriminance analysis can be performed. In particular during subsequent further use of the invention for communication after completion of the quantification of the perceptive faculty, a considerable saving of resources can be achieved in this way.

Figure 3:
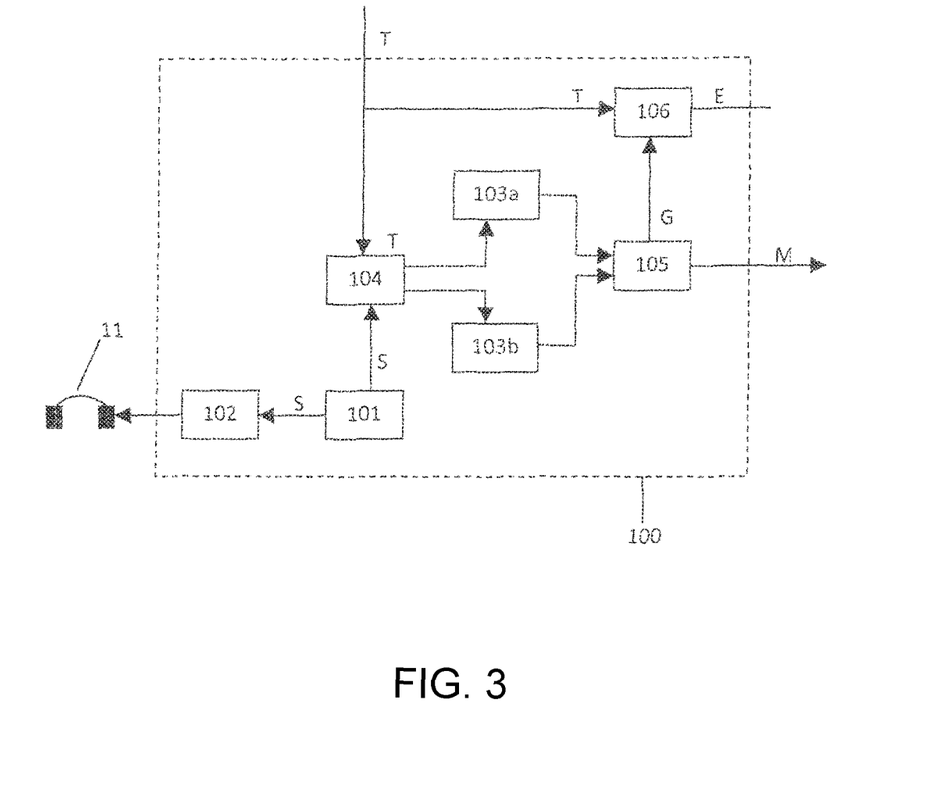
FIG. 3 shows in detail the control unit that is represented in FIG. 1.

The test values T obtained in the respective test step are assigned to the respective type of stimulus S. In the present example, a high-pitched sound is played with the headphones 11 as the stimulus S. The type of stimulus is transmitted to a memory control unit 104, which passes on the test value T to a first memory 103a for storage. If in a second or further test step a low-pitched sound is prescribed as the stimulus S, the memory control unit 104 passes on the test value T to a second memory 103b. At the end of the individual test steps, a large number of different test values T are present in each of the two memories 103a, 103b.

By means of discriminance analysis 105, to which the individual test values T that are stored in the memories 103a, 103b are fed, a distinguishing criterion G, which makes it possible to distinguish between the test values T that originate from the individual types of stimuli S, for example a high-pitched sound, and test values that originate from a low-pitched sound, can be determined. In addition, the discriminance analysis 105 also produces a measure M of the distinguishability of the test values T to be separated, which for the following reasons is regarded as a measure M of the perceptive faculty of the test subject 1.

If, for example, an EEG signal produced by the test subject 1 by thinking of the right hand after a high-pitched sound always leads to a test value T that corresponds to the distinguishing criterion G and a signal produced by the test subject 1 by thinking of the left hand after a low-pitched sound always leads to a test value T that does not correspond to the distinguishing criterion, the discriminance analysis 105 produces a maximum measure M of distinguishability. It can in this case be assumed that the test subject 1 concerned has understood the task and been able to perceive the individual applied stimuli S, and has reacted to them in a deliberately directed manner.

If, however, the respective test subject 1 has no perceptive faculty at all, different mental activities cannot be ascertained either. Even if the discriminance analysis 105 produces a distinguishing criterion G, no conclusion can be drawn in response to the respective stimulus S from the compliance or non-compliance with the distinguishing criterion G by the respective test value T. The measure M of distinguishability of the individual test values is consequently low.

For determining the individual values $g_a, \ldots, g_d$, w, s, that are used for the determination of the test values T, the following procedure can be adopted: starting from randomly prescribed starting values for the individual values $g_a, \ldots, g_d$, w, s, or starting from the starting values of already tested test subjects 1 with a high perceptive faculty, the individual data, specifically the weight vectors $g_a, \ldots, g_d$, the further weight vectors w and the further summand s, can be adapted until the discriminance analysis 105 produces a maximum measure of distinguishability on the basis of a first set of EEG data. The first set of EEG data does not necessarily have to contain all of the EEG data recorded from the test subject 1. It is quite possible that only some of the EEG data are used for determining the individual data $g_a, \ldots, g_d$, w, s. In order to be able to make better allowance for adaptation effects of the test subjects 1 to the respective task, the individual data $g_a, \ldots, g_d$, w, s may also be newly determined after particular time intervals. This is of advantage in particular whenever the method presented is used for communication after the quantification of the perceptive faculty.

This process of adaptation of the individual data $g_a, \ldots, g_d$, w, s can be iteratively repeated until there is an optimum distinguishability of the test values.

In principle, any optimizing method may be used for optimizing the individual values $g_a, \ldots, g_d$, w, s. The invention has achieved good results with a method that is known from the literature and the content of which is incorporated in this application:

Guger, C.; Ramoser, H.; Pfurtscheller, G., "Real-time EEG analysis with subject-specific spatial patterns for a brain-computer interface (BCI)," Rehabilitation Engineering, IEEE Transactions on, vol. 8, no. 4. pp. 447, 456, December 2000 doi: 10.1109/86.895947

The optimizing method may be controlled by an optimizing unit (not represented) of the control unit 10, which alters the individual individual values $g_a, \ldots, g_d$, w, s and in each case iteratively starts a renewed creation of the test data T by the test unit 20.

Different numerical methods may also be used for the discriminance analysis 105, in the present case the method described in "*C. M. Bishop, Neural Networks for Pattern Recognition, 1995: Clarendon*" being particularly suitable for linear discriminance analysis.

In order also to make it possible for the test subject 1 or a third party to carry out a visual check during the quantification method, after the respective test step the test value T determined in the test step may be subjected by a comparison unit 106 to the distinguishing criterion G determined from the discriminance analysis 105. The result E of the application of the criterion G to the test value T may be subsequently displayed to or otherwise brought to the knowledge of the test subject 1 or a third party. The result may for example be graphically presented on screens 12, 13. After a number of test steps, the discriminance analysis may also be carried out anew and the distinguishing criterion G newly established.

The determination of the distinguishing criterion G is not absolutely necessary for the quantification of the perceptive faculty, but may be used for determining the reaction of the test subject 1 in an individual case.

This fact is exploited by a particular development of the invention, which after the quantification of the perceptive faculty of the test subject 1 additionally strives for continual communication with the test subject 1.

After the quantification of the perceptive faculty of the test subject 1, the latter can be asked further questions for purposes of communication and the test subject 1 can be set mental activities that are to be performed when answering yes or no to this question. These questions may for example be displayed to the test subject 1 on his or her screen 12 or be transmitted by means of the headphones 11.

Here, the test subject 1 uses as the answer the same mental activities that were previously used when quantifying the perceptive faculty, since adequate distinguishability and a distinguishing criterion G for distinguishing the answers or the test values T has already been established with regard to these mental activities. The questions directed to the test subject 1 are normally questions that are provided with prescribed options for answers, for example the answers "YES" and "NO". It is also possible to agree with the test subject 1 a more complex range of answers comprising a greater number of distinguishable mental activities as answers, if they can be reliably and distinguishability ascertained.

Following individual questions, the test subject 1 performs mental activities, which are recorded by the EEG and classified by means of the previously determined discriminance analysis 105, i.e. the distinguishing criterion G originating from the discriminance analysis 105 is applied to the test value and the result E is determined. Depending on the result E, a different answer of the test subject 1 to the question asked is assumed. The answers or the determined results E of the classification are kept available for the questioner and displayed to him or her, and also possibly to the test subject, on the screens 12, 13.

In the above exemplary embodiment of the invention, a linear discriminance analysis was used by way of example for determining the measure M of distinguishability. However, this is not absolutely necessary. Rather, different types of classification analysis with which a separation of different test values is possible can be used. Thus, for example, support vector machines "*Hidden Markov model and support vector machine based decoding of finger movements using electrocorticography*; Wissel T, Pfeiffer T, Frysch R, Knight R T, Chang E F, Hinrichs H, Rieger J W, Rose G. *J Neural Eng.* 2013 October; 10(5):056020. doi: 10.1088/1741-2560/10/5/056020. Epub 2013 Sep. 18. PMID: 24045504 [PubMed—in process]" or neural networks "C. M. Bishop, *Neural Networks for Pattern Recognition*, 1995: Clarendon" may be used for the classification analysis in order to determine a measure M of distinguishability.

The measure M may also be determined by investigating with what probability the application of the classification analysis 105 to the individual EEG data assigned to the types of stimuli in each case suggests the correct stimulus. For this purpose, the classification analysis 105 is subsequently respectively applied individually to all of the determined EEG data, a classification result being determined in each case. It is subsequently investigated whether the respective classification result coincides with the stimulus that was applied to the patient during the determination of the EEG data. The ratio of the correct assessments to the total number of individual determined EEG data or the number of applied stimuli may be used as the measure M.

Evoked potentials are calculated by averaging the EEG data of a specific stimulus and are presented as an EP curve. The software overlays the evoked potentials of two classes and differences can therefore be easily detected. This on the one hand allows it to be seen whether the expected physiological response has occurred and also allows it to be detected whether differences exist. Furthermore, a statistical test is carried out, indicating whether the data are distinguishable. Statistically significant differences are marked in the presentation of the curve.

Event-related desynchronization is calculated for each class in that the data in a typical frequency range are filtered (for example alpha range 8-12 Hz, beta range 16-24 Hz, . . . ). After that, the power is calculated and these data are averaged over all the repeats. Subsequently, averaging in the time range is also carried out in order to smooth the curves. This changing of the power is related to a reference interval before the mental activity, and therefore indicates the change in the band power on account of the activity carried out. This result is also evaluated with a statistical test, so that only significant changes are presented.

Both event-related desynchronization and evoked potentials can be visually depicted and can serve the patient as feedback, in order that he or she carries out activities better. Whether the patient correctly performs the task constitutes important information for the operator, who can intervene in a corrective way. Furthermore, the operator can assess physiological effects on the basis of his or her experience.

The invention claimed is:

1. A method for quantifying the perceptive faculty of a person and for communicating with the person, the person being incapacitated and incapable of verbal communication, the method comprising:
   prescribing a set of at least two possible, differently perceptible types of stimuli to be applied to the person and subjecting the person to vibrations at different parts of the body and/or of differing intensity and/or duration, the vibrations being applied in vibration units each representing a respective one of the stimuli; and
   prompting the test subject to perform mental activities in a presence of a given stimulus according to a nature of the given stimulus;
   performing a plurality of test steps, and for each of the test steps:
      choosing a respective type of stimulus from the set of possible types of stimuli;
      applying a stimulus of the respectively chosen type of stimuli by applying a vibration unit to the person;
      within a given time range before, during or after the application of the respective stimulus, determining and recording EEG data of the person, and
      assigning respectively determined EEG data or data derived therefrom to the respective type of stimulus;
   using classification analysis to determine a measure of whether the EEG data assigned to a particular stimulus are distinguishable from the EEG data assigned to a stimulus of a different type; and
   using a measure of the distinguishability of the EEG data of different stimuli as a measure of the perceptive faculty that indicates an extent to which the person is still capable of communicating with the world around them;
   once the measure of the perceptive faculty has been determined, for purposes of communication, prompting the person to perform the mental activities that were previously used;
   wherein the person performs the mental activities in answer to a question asked;
   determining and recording EEG data of the person within prescribed time ranges during or after the question;
   classifying the respectively recorded EEG data by way of the classification analysis previously carried out; and
   using the respectively determined results of the classification as communication contents and keeping the results available.

2. The method according to claim 1, which comprises choosing the respective type of stimulus according to random criteria, setting the given time range to have a duration of 1 to 10 seconds, and prompting the person to answer yes and no to questions.

3. The method according to claim 1, which comprises determining the measure by investigating with what probability an application of the classification analysis to the individual EEG data assigned to the types of stimuli in each case suggests the correct stimulus.

4. The method according to claim 1, wherein the set of types of stimuli is prescribed by different sounds having differing duration, frequency and volume, in humanly audible frequencies and playing the respective sound to the person.

5. The method according to claim 1, wherein the set of types of stimuli comprises visual stimuli for one eye or both eyes and/or of differing intensity and/or duration, and the visual stimuli are applied to the person by way of a screen or by way of lighting means.

6. The method according to claim 1, wherein the set of types of stimuli comprises electrical stimuli to different parts of the body and/or of differing intensity and/or duration, and the electrical stimuli are applied to the person by means of electrical stimulators.

7. The method according to claim 1, which comprises, depending on the respective type of stimulus, prompting the person to one of the following mental activities, optionally when a vibration unit applies a tactile stimulus in a prescribed area of the body:
counting or calculating;
thinking of movements of body parts being extremities of a right or left half of the body.

8. The method according to claim 1, which comprises performing an assessment of the recorded EEG data, in that the individual EEG data of the individual EEG channels that were recorded at the same point in time are respectively combined to form a signal vector,
prescribing a plurality of weight vectors having a same number of elements as the signal vectors;
for each point in time, creating a respective scalar product of the determined signal vector with each of the weight vectors and assigning the respectively created scalar products to the respective weight vector;
determining, among the scalar products assigned to respectively the same weight vector, the variance over a prescribed time range and assigning the variance to the weight vector;
weighting the individual variances, and optionally a further, prescribed summand, with weight values of a further weight vector and summing the same; and
taking a sum thus obtained or a series of sums thus recorded directly one after another as a test value to form the basis for the classification analysis.

9. The method according to claim 8, which comprises prescribing four weight vectors.

10. The method according to claim 8, which comprises adapting the weight vectors and the weight values, and optionally the further summand, to the respective person, to thereby maximize the measure determined in the classification analysis.

11. The method according to claim 10, which comprises, starting from prescribed starting values, iteratively adapting the weight vectors, the weight values, and optionally the further summand, until the classification analysis on the basis of the already determined test data produces a maximum measure of distinguishability.

12. The method according to claim 10, which comprises, before the assessment by way of classification analysis, subjecting the EEG data channel by channel to a bandpass filtering, wherein the filtered signal contains frequencies between 8 Hz and 30 Hz.

13. The method according to claim 1, which comprises displaying the EEG data or the data taken as a basis for the classification analysis, the evoked potentials derived from the EEG data or the EEG data after carrying out an event-related desynchronization or the EEG data.

14. The method according to claim 13, which comprises displaying to the person and/or to an operator conducting the test.

15. The method according to claim 1, which comprises evaluating the EEG data with a statistical test and only displaying significant changes.

16. The method according to claim 1, which comprises carrying out the measure of whether the EEG data assigned to a particular stimulus are distinguishable from the EEG data assigned to a stimulus of a different type by way of one of the following types of classification analysis:
discriminance analysis;
linear discriminance analysis;
support vector machines;
neural networks.

17. The method according to claim 1, which comprises carrying out the method steps on a plurality of days and separately determining the measure of the perceptive faculty of the person for each day and using the measure that indicates the greatest perceptive faculty as the measure of the perceptive faculty of the person.

18. The method according to claim 17, which comprises carrying out the method steps on a plurality of successive days and repeatedly, and thereby using the same stimuli.

19. A non-transitory data carrier, comprising program code for carrying out the method according to claim 1 when the code is executed on a computer.

* * * * *